United States Patent
Garda et al.

(10) Patent No.: US 8,588,964 B2
(45) Date of Patent: Nov. 19, 2013

(54) STORAGE DEVICES, SYSTEMS, AND METHODS FOR DISPENSING MEDICATIONS

(75) Inventors: Laurie K. Garda, Oakmont, PA (US); Wendy Armstrong, Pittsburgh, PA (US); Amy Blew, Cranberry, PA (US); Jyotsna Rao, Pittsburgh, PA (US)

(73) Assignee: McKesson Automation Inc., Cranberry, PA (US)

( * ) Notice: Subject to any disclaimer, the term of this patent is extended or adjusted under 35 U.S.C. 154(b) by 230 days.

(21) Appl. No.: 13/075,670

(22) Filed: Mar. 30, 2011

(65) Prior Publication Data
US 2012/0253509 A1    Oct. 4, 2012

(51) Int. Cl.
*G06F 17/00*    (2006.01)
(52) U.S. Cl.
USPC ........... 700/240; 700/235; 700/236; 700/237; 700/242
(58) Field of Classification Search
USPC .................. 700/235, 236, 237, 240, 232, 242
See application file for complete search history.

(56) References Cited

U.S. PATENT DOCUMENTS

| | | | |
|---|---|---|---|
| 4,717,042 A | 1/1988 | McLaughlin | |
| 4,785,969 A | 11/1988 | McLaughlin | |
| 4,847,764 A | 7/1989 | Halvorson | |
| 5,014,875 A | 5/1991 | McLaughlin et al. | |
| 5,190,185 A | 3/1993 | Blechl | |
| 5,314,243 A | 5/1994 | McDonald et al. | |
| 5,346,297 A | 9/1994 | Colson, Jr. et al. | |
| 5,377,864 A | 1/1995 | Blechl et al. | |
| 5,405,048 A | 4/1995 | Rogers et al. | |
| 5,431,299 A | 7/1995 | Brewer et al. | |
| 5,460,294 A | 10/1995 | Williams | |
| 5,468,110 A | 11/1995 | McDonald et al. | |
| 5,480,062 A | 1/1996 | Rogers et al. | |
| 5,520,450 A | 5/1996 | Colson, Jr. et al. | |
| 5,564,803 A | 10/1996 | McDonald et al. | |
| 5,593,267 A * | 1/1997 | McDonald et al. | ........... 414/273 |
| 5,661,978 A | 9/1997 | Holmes et al. | |
| D384,578 S | 10/1997 | Wangu et al. | |
| 5,713,485 A | 2/1998 | Liff et al. | |
| 5,716,114 A | 2/1998 | Holmes et al. | |

(Continued)

OTHER PUBLICATIONS

"Institute for Safe Medication Practices (ISMP) 2008 Guidance on the Interdisciplinary Safe Use of Automated Dispensing Cabinets" [online] [Retrieved on Apr. 18, 2011]. Retrieved from the Internet: <http://www.ismp.org/tools/guidelines/ADC_Guidelines_Final.pdf>. 25 pages.

*Primary Examiner* — Timothy Waggoner
(74) *Attorney, Agent, or Firm* — Alston & Bird LLP

(57) ABSTRACT

Storage devices, systems, methods, and computer program products are provided for dispensing medication. The storage devices include a container dispensing device for providing users with containers that can be used to securely transport (i.e., in a closed, identifiable container) medications dispensed from the storage device for a single selected patient. In this way, a single user may be able to dispense medications for multiple patients during a single user interaction with a storage device, while keeping medications for different patients separate and easily identifiable so as to provide secure transport between the storage device and the different patients' bedsides. Thus, a printing device may be provided for printing a summary of details, such as in the form of a label and/or a receipt. A sensor may also be provided for detecting the receipt of medications into the container as a check that the correct medications were dispensed by the user.

22 Claims, 7 Drawing Sheets

(56) References Cited

U.S. PATENT DOCUMENTS

| | | |
|---|---|---|
| 5,745,366 A | 4/1998 | Higham et al. |
| 5,761,877 A | 6/1998 | Quandt |
| 5,797,515 A | 8/1998 | Liff et al. |
| 5,805,456 A | 9/1998 | Higham et al. |
| 5,842,976 A | 12/1998 | Williamson |
| 5,878,885 A | 3/1999 | Wangu et al. |
| 5,880,443 A | 3/1999 | McDonald et al. |
| 5,883,806 A | 3/1999 | Meador et al. |
| 5,893,697 A | 4/1999 | Zini et al. |
| 5,905,653 A | 5/1999 | Higham et al. |
| 5,912,818 A | 6/1999 | McGrady et al. |
| 5,927,540 A | 7/1999 | Godlewski |
| 5,940,306 A | 8/1999 | Gardner et al. |
| 5,971,593 A | 10/1999 | McGrady |
| 6,003,006 A | 12/1999 | Colella et al. |
| 6,011,999 A | 1/2000 | Holmes |
| 6,021,392 A | 2/2000 | Lester et al. |
| 6,039,467 A | 3/2000 | Holmes |
| 6,065,819 A | 5/2000 | Holmes et al. |
| 6,068,156 A | 5/2000 | Liff et al. |
| 6,109,774 A | 8/2000 | Holmes et al. |
| 6,112,502 A | 9/2000 | Frederick et al. |
| 6,116,461 A | 9/2000 | Broadfield et al. |
| 6,151,536 A | 11/2000 | Arnold et al. |
| 6,170,230 B1 | 1/2001 | Chudy et al. |
| 6,176,392 B1 | 1/2001 | William et al. |
| 6,189,727 B1 | 2/2001 | Shoenfeld |
| 6,223,934 B1 | 5/2001 | Shoenfeld |
| 6,256,967 B1 | 7/2001 | Hebron et al. |
| 6,283,322 B1 | 9/2001 | Liff et al. |
| 6,289,656 B1 | 9/2001 | Wangu et al. |
| 6,308,109 B1 * | 10/2001 | Yuyama et al. ............... 700/228 |
| 6,338,007 B1 | 1/2002 | Broadfield et al. |
| 6,339,732 B1 | 1/2002 | Phoon et al. |
| 6,361,263 B1 | 3/2002 | Dewey et al. |
| 6,370,841 B1 * | 4/2002 | Chudy et al. .................... 53/411 |
| 6,394,309 B1 * | 5/2002 | Fainberg ....................... 221/278 |
| 6,449,927 B2 | 9/2002 | Hebron et al. |
| 6,471,089 B2 | 10/2002 | Liff et al. |
| 6,497,342 B2 | 12/2002 | Zhang et al. |
| 6,499,270 B2 | 12/2002 | Peroni et al. |
| 6,532,399 B2 | 3/2003 | Mase |
| 6,564,121 B1 | 5/2003 | Wallace et al. |
| 6,581,798 B2 | 6/2003 | Liff et al. |
| 6,588,548 B1 * | 7/2003 | Dewitt .............................. 186/2 |
| 6,609,047 B1 | 8/2003 | Lipps |
| 6,611,733 B1 | 8/2003 | De La Huerga |
| 6,625,952 B1 | 9/2003 | Chudy et al. |
| 6,640,159 B2 | 10/2003 | Holmes et al. |
| 6,650,964 B2 | 11/2003 | Spano, Jr. et al. |
| 6,671,579 B2 | 12/2003 | Spano, Jr. et al. |
| 6,681,149 B2 | 1/2004 | William et al. |
| 6,742,671 B2 | 6/2004 | Hebron et al. |
| 6,755,931 B2 | 6/2004 | Vollm et al. |
| 6,760,643 B2 | 7/2004 | Lipps |
| 6,776,304 B2 | 8/2004 | Liff et al. |
| 6,785,589 B2 | 8/2004 | Eggenberger et al. |
| 6,790,198 B1 | 9/2004 | White et al. |
| 6,814,254 B2 | 11/2004 | Liff et al. |
| 6,814,255 B2 | 11/2004 | Liff et al. |
| 6,847,861 B2 | 1/2005 | Lunak et al. |
| 6,874,684 B1 | 4/2005 | Denenberg et al. |
| 6,892,780 B2 | 5/2005 | Vollm et al. |
| 6,895,304 B2 | 5/2005 | Spano, Jr. et al. |
| 6,975,922 B2 | 12/2005 | Duncan et al. |
| 6,985,797 B2 | 1/2006 | Spano, Jr. et al. |
| 6,996,455 B2 | 2/2006 | Eggenberger et al. |
| 7,010,389 B2 | 3/2006 | Lunak et al. |
| 7,014,063 B2 | 3/2006 | Shows et al. |
| 7,016,766 B2 | 3/2006 | William et al. |
| 7,040,504 B2 * | 5/2006 | Broadfield et al. ........... 700/236 |
| 7,052,097 B2 | 5/2006 | Meek, Jr. et al. |
| 7,072,737 B2 | 7/2006 | Lunak et al. |
| 7,072,855 B1 | 7/2006 | Godlewski et al. |
| 7,077,286 B2 | 7/2006 | Shows et al. |
| 7,085,621 B2 | 8/2006 | Spano, Jr. et al. |
| 7,092,796 B2 | 8/2006 | Vanderveen |
| 7,093,755 B2 | 8/2006 | Jordan et al. |
| 7,100,792 B2 | 9/2006 | Hunter et al. |
| 7,103,419 B2 | 9/2006 | Engleson et al. |
| 7,111,780 B2 | 9/2006 | Broussard et al. |
| 7,139,639 B2 | 11/2006 | Broussard et al. |
| 7,150,724 B2 | 12/2006 | Morris et al. |
| 7,171,277 B2 | 1/2007 | Engleson et al. |
| 7,194,333 B2 * | 3/2007 | Shoenfeld ..................... 700/243 |
| 7,218,231 B2 | 5/2007 | Higham |
| 7,228,198 B2 | 6/2007 | Vollm et al. |
| 7,249,688 B2 | 7/2007 | Hunter et al. |
| 7,348,884 B2 | 3/2008 | Higham |
| RE40,453 E * | 8/2008 | Lasher et al. ................. 221/174 |
| 7,417,729 B2 | 8/2008 | Greenwald |
| 7,419,133 B2 | 9/2008 | Clarke et al. |
| 7,426,425 B2 | 9/2008 | Meek, Jr. et al. |
| 7,427,002 B2 * | 9/2008 | Liff et al. ...................... 700/232 |
| 7,430,838 B2 * | 10/2008 | Rice et al. ...................... 700/244 |
| 7,554,449 B2 | 6/2009 | Higham |
| 7,571,024 B2 | 8/2009 | Duncan et al. |
| 7,588,167 B2 | 9/2009 | Hunter et al. |
| 7,857,161 B2 * | 12/2010 | Pinney et al. ................. 700/242 |
| 8,260,632 B2 * | 9/2012 | Moncrief et al. ................. 705/2 |

* cited by examiner

STORAGE DEVICES, SYSTEMS, AND METHODS FOR DISPENSING MEDICATIONS

BACKGROUND

Automated dispensing cabinets (ADCs) are commonly used in healthcare facilities, such as hospitals, to provide healthcare professionals, such as nurses, with automated access to medication without requiring the pharmacy to fill patient-specific cassettes of unit-dose medications, which would then have to be delivered to the particular nursing unit and stored in non-automated medication cabinets or carts. In contrast, ADCs are computerized drug storage devices that allow nurses to automatically dispense medications to fill prescriptions near point of care, while at the same time tracking and controlling drug distribution.

Although ADCs have provided nurses with quicker and easier access to a patient's medications, the increasing numbers of patients who are admitted to healthcare facilities each year, coupled with the budgetary constraints on hiring additional healthcare professionals to care for these patients, puts pressure on nurses to multi-task when performing certain work functions so as to have as much time as possible to directly interact with patients. It is, therefore, becoming more commonplace for nurses to dispense medication for more than one patient during a single interaction with an ADC in order to avoid multiple trips to the ADC over a given time period. This creates the potential for errors when administering the medication to the patients. In other words, because at any given time the nurse may be carrying multiple medications for multiple patients with different conditions, there is a risk that the wrong medication may be given to the wrong patient.

Accordingly, there is a need in the art for an improved system and method for dispensing medication that allows healthcare professionals to securely transport dispensed medication so as to minimize the risk of inaccurately administering the medication.

BRIEF SUMMARY OF THE INVENTION

Storage devices, systems, methods, and computer program products are therefore provided for dispensing medication. Embodiments of the storage devices, systems, methods, and computer program products provide users with a way to dispense medications for multiple patients during a single user interaction with a storage device, while at the same time keeping medications for different patients separate and easily identifiable so as to provide secure transport between the storage device and the different patients' bedsides.

In one exemplary embodiment, a storage device for dispensing medication is provided. The storage device may be configured to dispense medications during multiple dispensing transactions conducted for a single user during a single interaction, and each dispensing transaction may be associated with a particular selected patient. The storage device may comprise a plurality of drawers, a display device, a user input device, and a container dispensing device. The drawers may be defined by the storage device and may be configured to store a plurality of medications. The display device may be associated with the storage device and may be configured to present medication dispensing information related to a selected patient. The user input device may be associated with the storage device and may be configured to receive input from a user regarding at least one dispensing transaction. Furthermore the container dispensing device may be supported by the storage device and may be configured to store and dispense containers. Each container may be configured to receive a plurality of dispensed medications for administering to a single selected patient, and each container may be configured to allow secure transport of the dispensed medications received therein between the storage device and the selected patient.

In some cases, the storage device may further comprise a printing device configured to print a summary of a selected dispensing transaction. The summary may comprise at least one detail relating to the selected dispensing transaction, and the at least one detail may be selected from the group consisting of a name of the selected patient, a birth date of the selected patient, a location of the selected patient, a date of the selected dispensing transaction, a time of the selected dispensing transaction, and a listing of the dispensed medications received within the container. In some cases, the summary may be embodied by a label comprising a printed surface and an adhesive surface, and the adhesive surface may be configured to be applied to an outer surface of the container. For example, each container may comprise a bag, and the label may be configured to be applied to the bag so as to seal the medications received therein. In other cases, the summary may be embodied by a receipt, and each container may be configured to receive the receipt therein. Each container may be made of a translucent material and/or may define an open end, wherein the open end is sealable onto itself.

In some embodiments, the storage device may further comprise a sensor configured to detect receipt of the dispensed medications within the container. In addition, at least one of the dispensed medications may be a medical accessory.

In other embodiments, a system for dispensing medications is provided. The system may include a processor configured to direct the dispensing of medications from a storage device during at least one dispensing transaction conducted for a single user during a single interaction. Each dispensing transaction may be associated with a particular selected patient, and the processor may be further configured to access medication dispensing information related to the selected patient. The system may further include a display device in communication with the processor, a user input device in communication with the processor, and a sensor in communication with the processor. The display device may be configured to present to the user at least one detail from the accessed medication dispensing information. The user input device may be configured to receive input from the user regarding the accessed medication dispensing information. Furthermore, the sensor may be configured to detect receipt of at least one dispensed medication within a container, and each container may be configured to receive a plurality of dispensed medications for administering to the selected patient. Each container may be configured to allow secure transport of the dispensed medications received therein from a storage device, from which the medication was dispensed, to the selected patient. In some cases, the processor may be configured to determine an accuracy of the dispensing transaction based on the receipt of the at least one dispensed medication detected by the sensor.

The system may further include a printing device in communication with the processor and configured to print a summary of a selected dispensing transaction. The summary may comprise at least one detail relating to the selected dispensing transaction. The summary may, in some cases, be embodied by a label comprising a printed surface and an adhesive surface, wherein the adhesive surface is configured to be applied to an outer surface of the container. Each container may comprise a bag, and the label may be configured to be applied to the bag so as to seal the received medications therein. In other cases, the summary may be embodied by a receipt, and each container may be configured to receive the receipt therein.

In still other embodiments, a method and a computer program product for dispensing medications are provided. The method and computer program product receive input regarding medication dispensing information related to a selected patient via a user input device, provide access to a container configured to receive a plurality of dispensed medications for administering to the selected patient, and provide a user with access to dispense at least one medication stored in a storage device and prescribed to the selected patient such that the user is able to place at least some of the dispensed medications into the container for administering to the selected patient. Each container may be configured to allow secure transport of the dispensed medications received therein from the storage device to the selected patient.

In some cases, access to a container may be provided by, for example, prompting the user to dispense one of a plurality of containers from a container dispensing device. Also, a summary of the medication dispensing information related to the selected patient may be printed. Furthermore the receipt of the dispensed medications into the container may be sensed. In addition, an accuracy of the dispensing transaction may be determined based on the sensed receipt of the dispensed medications.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

DETAILED DESCRIPTION

Figure 1:
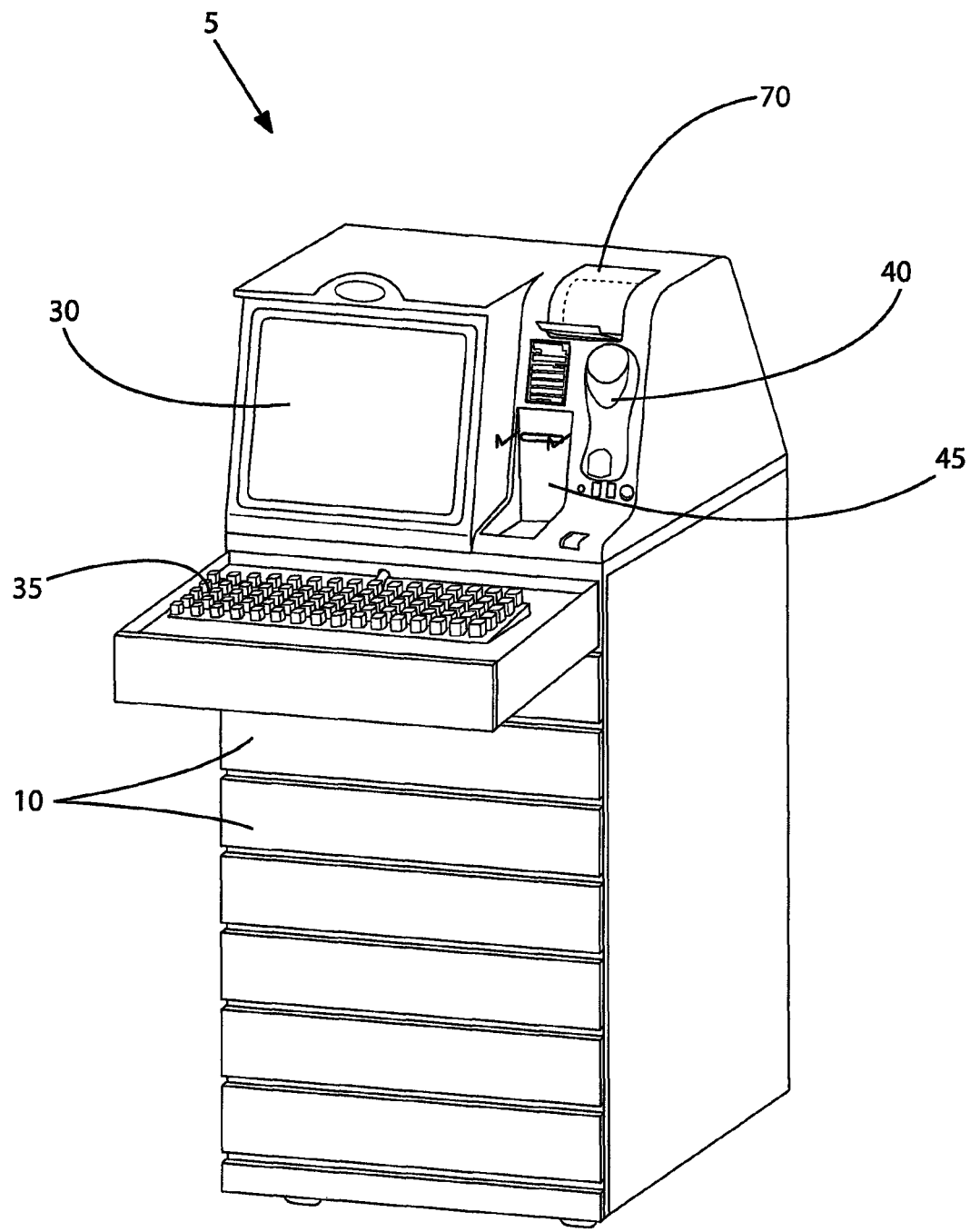
FIG. 1 illustrates an automated storage device in accordance with one exemplary embodiment.

Embodiments of the present inventions now will be described more fully hereinafter with reference to the accompanying drawings, in which some, but not all embodiments of the inventions are shown. Indeed, embodiments of these inventions may be embodied in many different forms and should not be construed as limited to the embodiments set forth herein; rather, these embodiments are provided so that this disclosure will satisfy applicable legal requirements. Like reference numerals refer to like elements throughout.

The storage devices, systems, and methods of embodiments of the present invention may be used by healthcare facilities, such as hospitals, physicians' offices, healthcare clinics, and any other facility that manages and/or dispenses drugs for patient use. The storage devices, systems, and methods described herein provide a more streamlined and efficient way for healthcare professionals to interface with an automated storage device, such as an automated dispensing cabinet (ADC), to dispense medications. Although nurses are often tasked with accessing medication stored in an automated storage device, and the example of a nurse is used in the description that follows, it is understood that the described embodiments apply to any user who is interfacing with the automated storage device, including physicians, pharmacists, nurses, laboratory personnel, respiratory therapists, and others. Furthermore, although the example of a user interfacing with an automated storage device for the purpose of dispensing medications to administer to patients is predominantly described below, one skilled in the art in light of this disclosure would recognize that the embodiments are also applicable to users interfacing with the automated storage device for the purpose of restocking medication, taking inventory, and performing other tasks that may require access to the medication stored in the automated storage device. In addition, the term "automated storage devices" is intended to include any type of automated storage device, including automated dispensing cabinets (ADCs), unit-based cabinets (UBCs), automated dispensing devices (ADDs), automated distribution cabinets, and automated dispensing machines (ADMs), among others.

The Institute for Safe Medication Practices (ISMP) is a pubic charity that is devoted to medication error prevention and safe medication use. This organization is viewed as a resource by healthcare facilities for providing impartial, timely, and accurate medication safety information and recommendations. See, e.g., www.ismp.org.

The ISMP recommends the secure transportation of medications from automated storage devices to patients' bedsides to minimize the risk of medications being administered to the wrong patient and/or at the wrong time. One suggestion offered by the ISMP is to hand-carry a single patient's medications for one administration time from the storage device directly to the patient's bedside. In cases where more than one patient's medications must be transported, the use of computers on wheels (COWs), mobile carts, or workstations on wheels (WOWs), which provide labeled, lockable patient-specific drawers, is recommended. The transport of medications in clothing pockets, attached to clipboards, inside of medical records, or in Medication Administration Record (MAR) binders is expressly discouraged. See ISMP Core Process #10.

It is often too expensive for a healthcare facility to provide additional automated storage devices, which would allow nurses to more easily adhere to the ISMP's recommendation to hand-carry a single patient's medications for one administration time from the storage device to the patient's bedside. The limited numbers of storage devices and their being located far from some patients' rooms makes it more likely that some nurses will adopt discouraged practices involving the dispensing of medications for multiple patients during a single interaction with a storage device. Similarly, the cost associated with obtaining COWs, mobile carts, and WOWs makes it difficult to abide by the ISMP's recommendations for secure transport when multiple patients' medications are dispensed. The use of COWs, mobile carts, and WOWs provides additional challenges, as these devices often require batteries to be charged and need sufficient space to be maneuvered easily through hallways and patient rooms, as well as sufficient storage space when not used. As a result, many nurses resort to exactly the behaviors that are discouraged by the ISMP in order to make more efficient use of their time and have more time to spend at patients' bedsides—the nurses will put medications in clothing pockets; place them in open, unlabeled containers, such as paper cups; attach them to clipboards; or transport them inside of medical records and MAR binders.

Turning now to FIG. 1, an automated storage device 5 is shown. The storage device 5 may be configured to store a number of different types and quantities of medications. In this regard, the storage device 5 may include (e.g., define) a plurality of drawers 10. Different types of storage devices 5 may include different sizes and styles of drawers 10, depending on the types of medications to be stored in the drawers, the quantities required (which may be dictated by the size of the facility), and user preferences. For example, some drawers 10 may be deep, whereas others may be shallower. In addition, access to the drawers 10 may be restricted to certain authorized users and may further be accessible only when medication stored in the particular drawer is to be dispensed, as described in greater detail below. Accordingly, each drawer 10 may be in a locked state until an authorized user interfaces with the storage device 5 to select for dispensing a particular medication stored within a particular drawer, at which point the storage device may unlock and/or open the drawer containing the selected medication to allow the user's access.

The drawers 10 may hold more than just medications, in some cases. For example, certain medical accessories or supplies may also be stored in the automated storage device 5, such as applicators, syringes, keys, prescription pads, cameras, etc., which may also be dispensed by the nurse during an interaction with the storage device. Accordingly, although the examples provided below refer to the dispensing of medications, the dispensing and transport of any item stored in the storage device 5, such as medical accessories, is contemplated herein.

In some embodiments, the storage device 5 further includes a display device 30 and a user input device 35 that are mounted to or otherwise associated with the storage device. The display device 30 may be a monitor, as depicted, and may be configured to present various items of medication dispensing information related to a selected patient for the user to view, as described below. For example, the user may be able to view medication dispensing information regarding the patients assigned to a particular nurse's shift or other patients to whose records the nurse has access, as well as medication dispensing information relating to the medications stored in the storage device 5 and/or other storage devices in communication with the storage device 5.

For example, the user may be able to view a list of patients under the user's care; view patient details (e.g., patient's name, date of birth, medical condition, allergies, date of admittance, date of expected discharge, etc.); view a list of prescribed medications for a particular patient; view medication details (such as potential interactions, medication properties, and dosage information); and/or view order details (such as the name of a medication, required dosage, quantity to be dispensed, location of the medication in the storage device (drawer and pocket), etc.).

Similarly, the user input device 35 may be configured to receive input from the user regarding at least one dispensing transaction. In this regard, the term "dispensing transaction" is used herein to describe the interfacing between the user and the storage device to dispense one or more medications to be administered to a single patient. Thus, each dispensing transaction is associated with a particular selected patient. Furthermore, each user may have multiple dispensing transactions with the storage device in a single interaction with the storage device. In this regard, the window between the time a user logs into the system (e.g., provides identification credentials indicating that the user is authorized to have access to the medications stored within the storage device) to the time the user logs out of the system (which would require another log-in by the same or a different user for access to the storage device) may define the interaction, whereas the time it takes for the user to dispense medications relating to a particular patient may define the dispensing transaction. Thus, a user may have multiple dispensing transactions for one or more patients in a single user interaction with the storage device.

With continued reference to FIG. 1, the user input device 35 may be configured to receive user input regarding a particular dispensing transaction. For example, the user input device 35 may receive input in the form of identification credentials authorizing the user to access the storage device 5 or a particular drawer 10 of the storage device; a selection of a patient for whom medication is to be dispensed; a request for information regarding a particular medication stored in one of the drawers or a particular patient to whose records the user has access; a selection of a particular medication to be viewed or dispensed; and so on. As another example, the user input device 35 may be configured to receive user input regarding an inventory of a particular drawer 10 or multiple drawers, such as a count of the medications remaining in a particular drawer or pocket of the drawer after a medication has been dispensed. Furthermore, in some cases, the storage device 5 may be configured to communicate with other storage devices in other parts of the healthcare facility, such that the user may be able to enter input requesting information regarding the contents of the other storage devices.

In some cases, more than one user input device may be provided. For example, in the depicted embodiment, the storage device 5 includes both a user input device 35 in the form of a keyboard and an additional user input device 40 in the form of a barcode reader. The barcode reader may be configured to scan barcodes off medication packaging, and/or the barcode reader may be configured to read a user's identification credentials (e.g., badge, bracelet, key, etc.) to ascertain whether the user has access to a particular storage device and/or access to a particular medication, as well as to track and trend access to the storage device, such as for taking inventory and generating reports regarding users. Other examples of user input devices may include a mouse and a touch screen, among others. Furthermore, in some cases, both the display device 30 and the user input device 35, 40 are embodied in the same device, such as when the monitor is a touch screen that is configured to receive input via a user's touch selections of options that are presented on the screen.

Referring again to FIG. 1, the storage device 5 may also include a container dispensing device 45 mounted to or otherwise supported by the storage device. The container dispensing device 45 may be configured to store and dispense containers, and each container may be configured to receive one or more dispensed medications for administering to a single selected patient. Thus, each container may be configured to allow the secure transport of the dispensed medications received therein between the storage device 5 and the selected patient's bedside.

Figure 3:
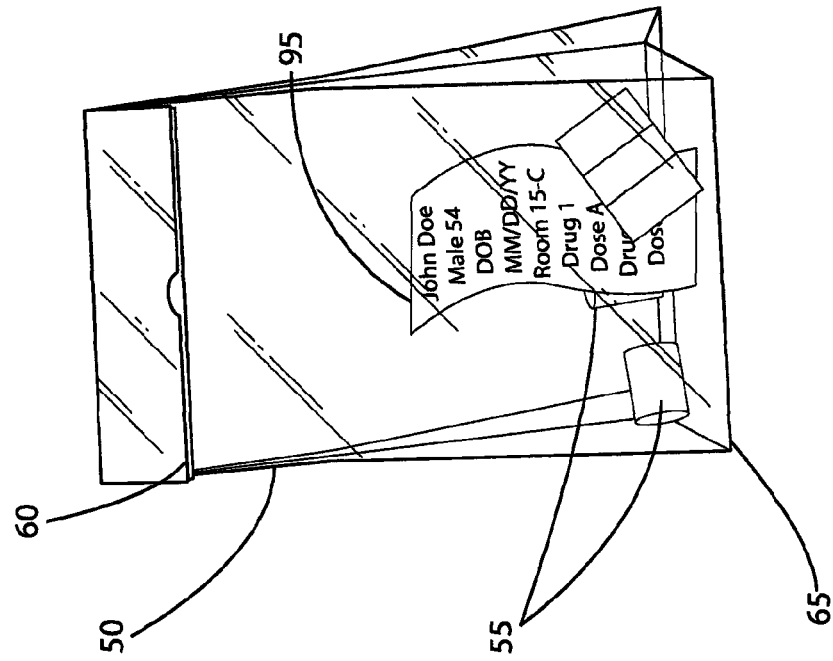
FIG. 3 illustrates a container with a receipt in accordance with another exemplary embodiment of the present invention.
Figure 2:
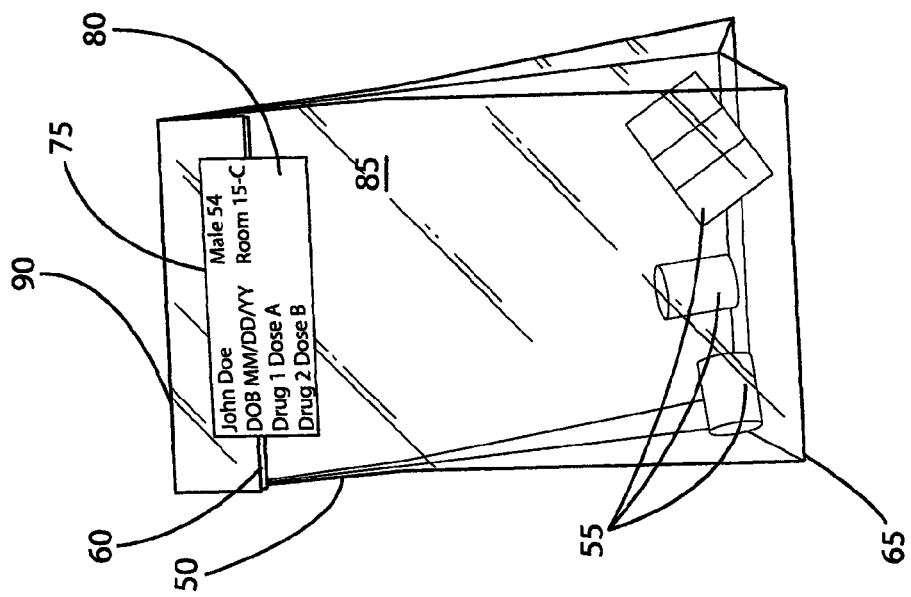
FIG. 2 illustrates a container with a label in accordance with one exemplary embodiment of the present invention.

Turning now to FIGS. 2 and 3, the container 50 may be any type of container that can be closed or sealed such that medications 55 received therein may be securely transported between the storage device 5 and the patient's bedside or another location, thereby minimizing the risk of improper administration to the selected patient and providing for secure transport of medication. In some cases, for example, the container 50 may be a rigid container, such as in the form of a box or cylinder, and in other cases the container may be a bag, as in the depicted embodiment of FIGS. 2 and 3. In this regard, the container 50 may be made of any suitable material, such as plastic, paper, cardboard, fabric, etc., and may include an open end 60 and a closed end 65, as shown. The open end 60 may be sealable onto itself, such as via a layer of adhesive applied to one or more surfaces of the open end, a tongue and groove closure feature formed at the open end, or some other feature allowing the open end to be closed by the user once the medications dispensed in a dispensing transaction for a selected patient have been deposited in the container 50. Furthermore, the container 50 may be either opaque, such that the contents therein cannot be observed through the material of the container, or translucent, such that the contents are at least partially visible through the material of the container.

Figure 4:
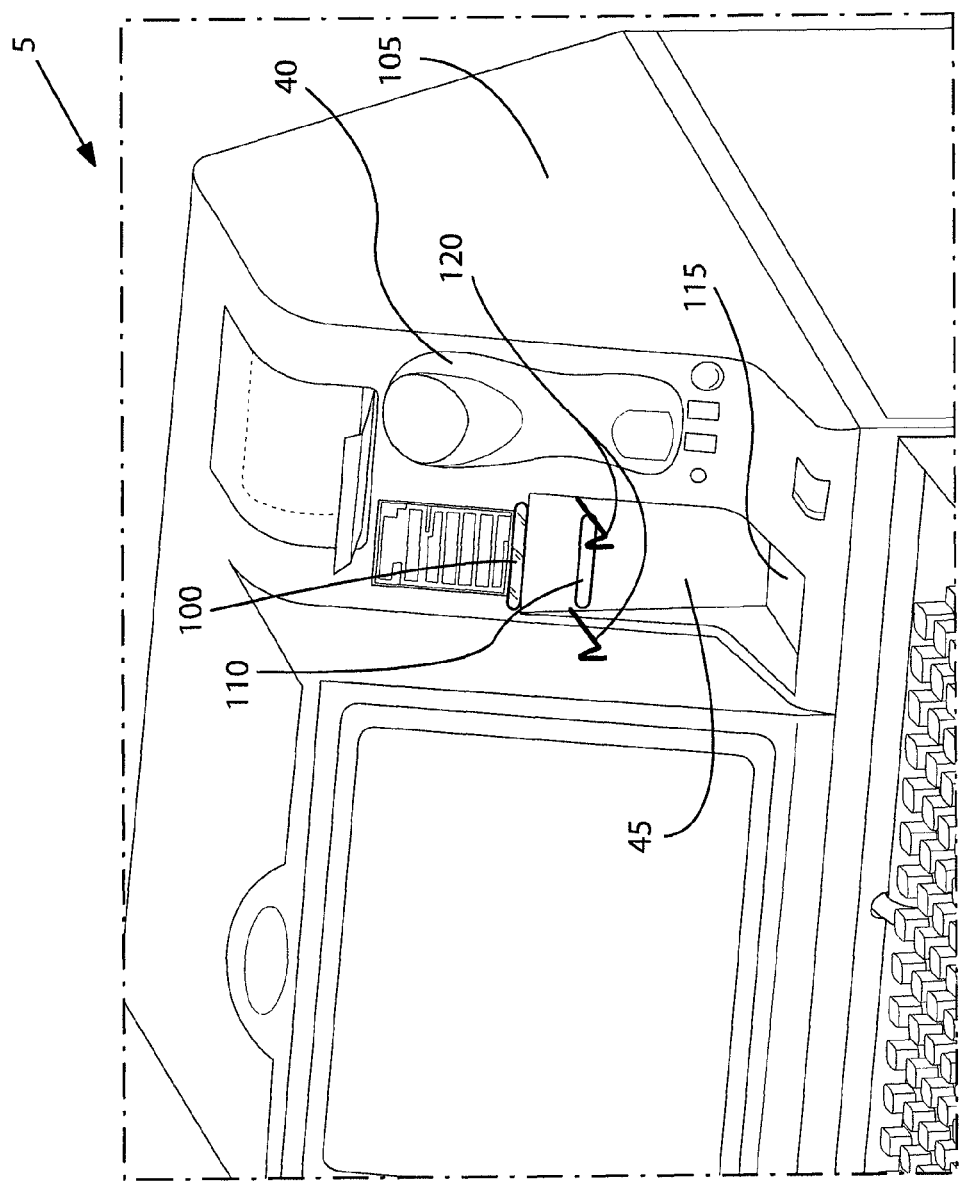
FIG. 4 illustrates a close-up view of a container dispensing device of the storage device of FIG. 1 in accordance with one exemplary embodiment of the present invention.
Figure 4A:
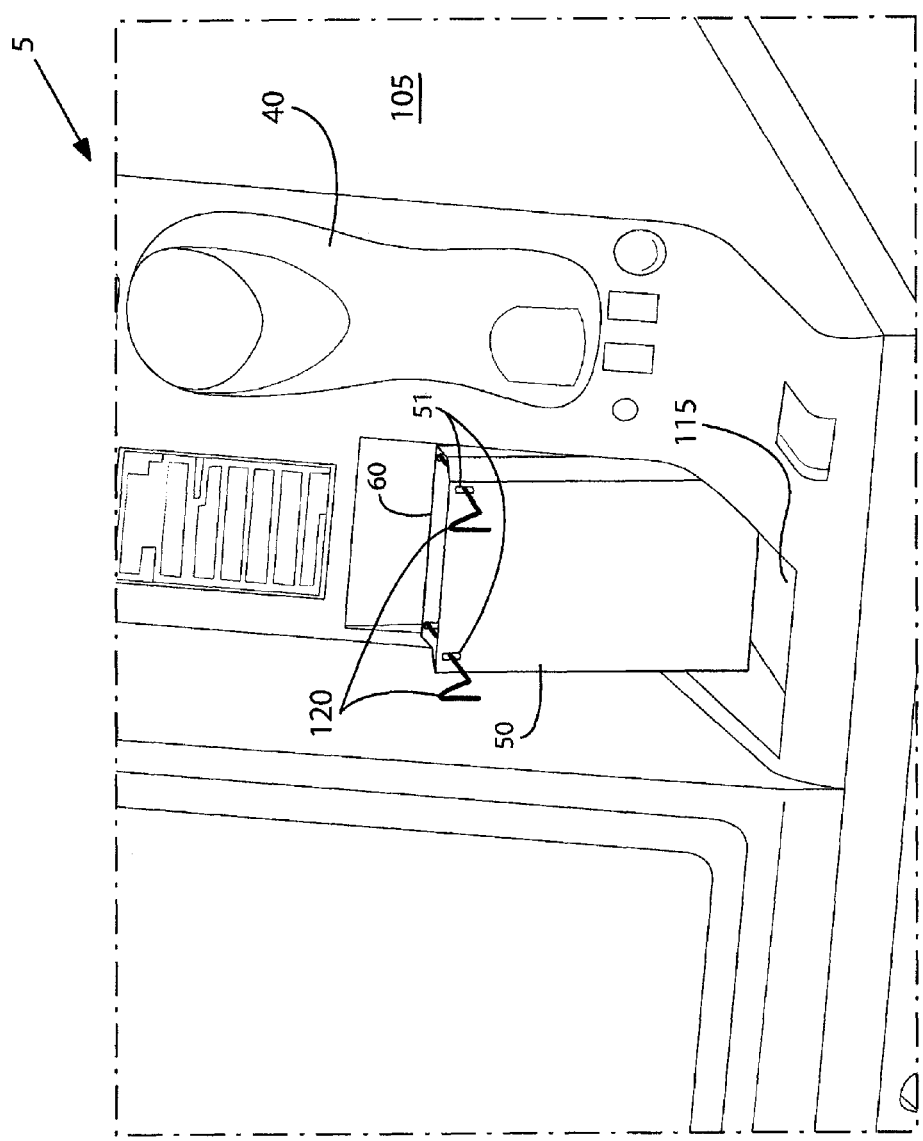
FIG. 4A illustrates a close-up view of the container dispensing device of FIG. 4 with a bag positioned to receive medications.
Figure 5:
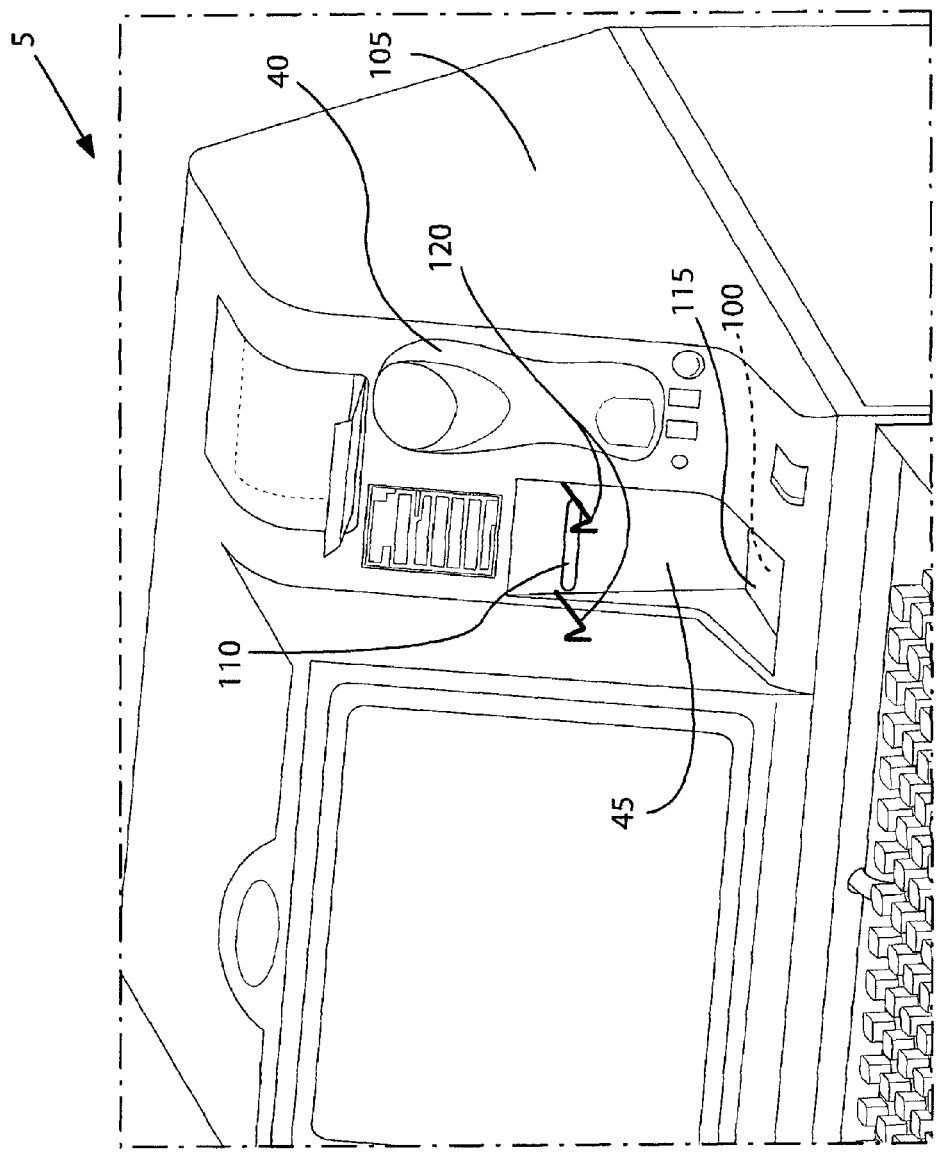
FIG. 5 illustrates a close-up view of a container dispensing device of the storage device of FIG. 1 in accordance with another exemplary embodiment of the present invention.

In some cases, the storage device 5 may include one or more structures that are configured to cooperate with corresponding structures of the container 50 to support or hold the container while the user is dispensing medications and depositing them into the container during a dispensing transaction. With reference to FIGS. 4, 4A, and 5, the container dispensing device 45 may be a compartment defined within a housing 105 of the storage device 5, and the dispensing device may include a slot 110 (e.g., defined by the housing) via which each container 50 is accessible for removal and use. The housing 105 of the storage device 5 may include a platform 115 configured to support the container 50 after the user has dispensed the container from the container dispensing device 45. The user may place the empty container 50 on the platform 115 while the user is continuing to interface with the storage device 5 to dispense medications. The container 50 may, for example, be structured to have a flat bottom or otherwise be configured such that the container is able to support itself in an open position when placed on the platform 115.

Alternatively or in addition, such as in cases where the container 50 is a bag, the container dispensing device 45 may further include support arms 120 configured to hold the dispensed bags while the user is dispensing medications and depositing the medications into the bag. The support arms 120 may, for example, be configured to be passed through one or more holes 51 defined in the bag, as shown in FIG. 4A, such that with the bag 50 supported by the support arms via the holes, the open end 60 of the bag is open to receive medications. The closed end of the bag may in some cases rest on the platform 115 for additional support.

Referring again to FIG. 1, in some embodiments, the storage device 5 may include a printing device 70 that is configured to print a summary of a selected dispensing transaction. The summary may include, for example, one or more details relating to the selected dispensing transaction. Such details may include the name of the selected patient, the selected patient's identification number, any patient-specific information (such as any allergies or special considerations) a location of the selected patient (e.g., the patient's room number, the nursing unit in which the patient is being held, the patient's bed number, etc.), the date of the selected dispensing transaction (e.g., the date on which the medications in the bag were dispensed), the time of the selected dispensing transaction (e.g., the time at which the medications were dispensed), and/or a listing of the dispensed medications received within the container (e.g., a list of the medications dispensed during the particular dispensing transaction, the associated doses, notes on drug interactions, any information regarding how to administer the medication to the selected patient, such as how many times a day or by what route, etc.).

In some cases the summary may be a label 75 that includes a printed surface 80 and an adhesive surface (not visible). The adhesive surface may, for example, be coated with an adhesive, and a lining may be provided on the adhesive surface when the label 75 is first printed out. The user may thus retrieve the label from the printer, visually check that the appropriate information was printed upon the printed surface 80, remove the lining, and apply the adhesive surface to an outer surface 85 of the container to affix the label to the container. In cases where the container 50 is a bag, for example, as depicted in FIG. 2, the label 75 may be used to seal the medications 55 received therein. For example, the user may deposit the medications 55 into the bag 50, fold the bag over onto itself proximate the open end 60 to create a creased closed end 90, then apply the label 75 to the open end to maintain the bag in the closed position, as shown.

Alternatively, the summary may be a receipt 95, and each container 50 may be configured to receive the receipt therein, as shown in FIG. 3. In this case, the printing device 70 (shown in FIG. 1) may be configured to print out the receipt 95 as described above, and the user may remove the receipt from the printing device (e.g., by cutting the receipt along an edge of the printing device to separate the receipt from a roll of paper). The user may then drop the receipt 95 into the container (e.g., into the bag) and seal the medications 55 and the receipt within the container in any of the ways described above. In this way, once the user arrives at the patient's bedside and accesses the contents of the container, the user can easily refer to the receipt 95 for information regarding the dispensed medications or any other aspect of the dispensing transaction recorded on the receipt. In some cases, both a receipt 95 and a label 70 may be provided for each container, either by default or upon a user's specific request.

In some embodiments, the storage device 5 further comprises a sensor 100 that is configured to detect the receipt of the dispensed medications 55 within the container 50, as shown in FIG. 4. The sensor 100 may be, for example, an optical sensor disposed proximate the support arms 120, such that when a container 50 (e.g., a bag defining holes near its open end) is placed onto the support arms, the open end of the container is located near the optical sensor. In this way, each time a user places a medication into the container, the user's hand should disrupt the field generated by the optical sensor 100, and the sensor should in turn detect that a medication has been placed in the container.

In some cases, the optical sensor 100 may be associated with a barcode reader or RFID reader that is configured to detect each medication 55 (e.g., by sensing a barcode or RFID tag on the medication packaging) as the medication is placed in the container. In other cases, however, an optical sensor 100 may not be required, and a user input device 40 in the form of a barcode reader (depicted in FIG. 1) may serve as the sensor. For example, after dispensing each medication, the user may manually scan the dispensed medication at the barcode reader 40 and then place the scanned medication into the container 50 supported on the platform 115. By scanning the medication prior to depositing the medication into the container, the user may be able to verify that the correct medication was dispensed from the storage device 5. In other words, the storage device (e.g., a processor of the storage device, described below) may be able to verify that the medication that was dispensed by the user and presumably put in the container for administering to the selected patient matches the ordered medication that the user was directed to dispense.

In other embodiments, illustrated in FIG. 5, the sensor 100 may be a scale that is embedded in or otherwise associated with the platform 115. Thus, as medications are placed into the container, the sensor 100 in this case may be able to determine whether the dispensed medication has been placed into the container based on the total weight of the container and its contents (e.g., as compared to an estimate of what the container should weigh with the dispensed medication included therein). For example, in cases where the container 50 is a bag and the container dispensing device 45 includes support arms 120, as described above, the bag may be supported by the support arms via holes defined near the open end of the bag, keeping the bag in the open position. The closed end of the bag may in turn rest on the platform 115 such that, as additional medications are placed in the bag, the sensor 100 can detect a cumulative weight of the bag with the contents therein.

Figure 6:
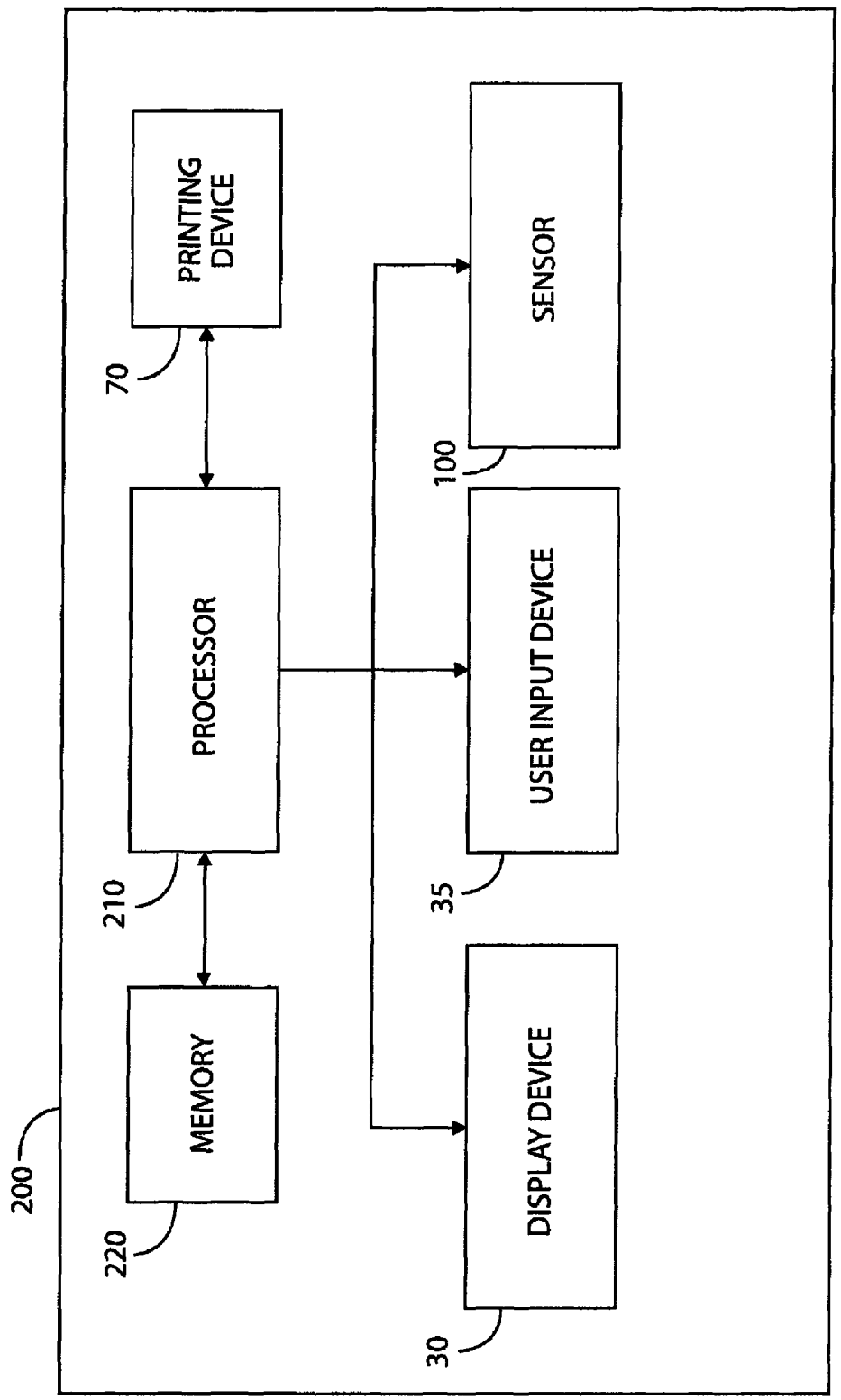
FIG. 6 is a schematic representation of a system for dispensing medications according to an exemplary embodiment of the present invention.

Referring now to FIG. 6, embodiments of system 200 for dispensing medication may be provided (for example, in a storage device) that include a processor 210, a display device 30 in communication with the processor, a user input device 35 in communication with the processor, and a sensor 100 in communication with the processor. The processor 210 may be configured to direct the dispensing of medications from an associated storage device during at least one dispensing transaction conducted for a single user during a single transaction with the storage device, each dispensing transaction being associated with a particular selected patient, as described above. In this regard, the processor 210 may be configured to access medication dispensing information related to the selected patient.

Figure 7:
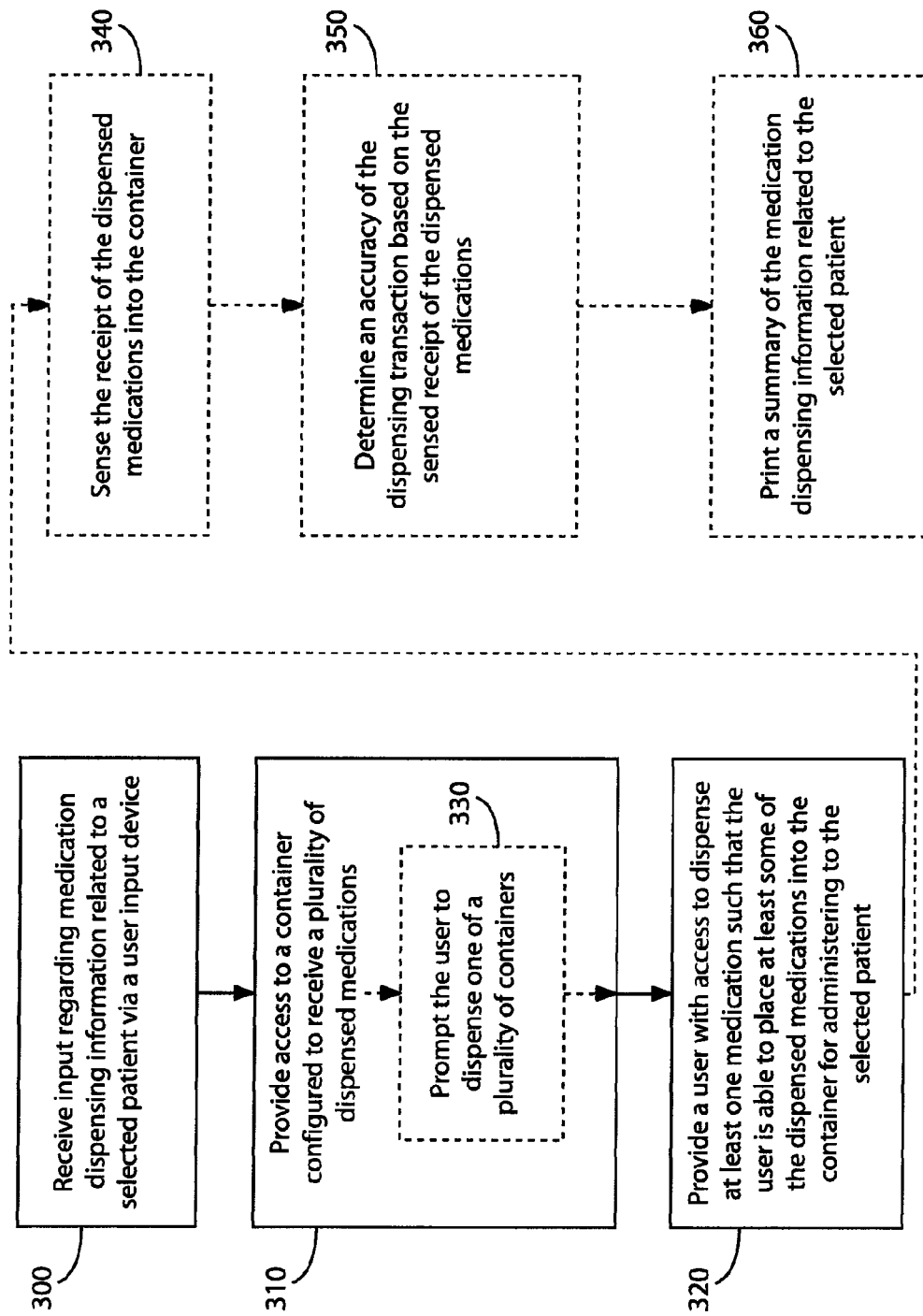
FIG. 7 is a flow chart illustrating a method of dispensing medications according to an exemplary embodiment of the present invention.

As described above, and with reference to FIG. 7, the display device 30 may be configured to present to the user at least one detail from the accessed medication dispensing information, and the user input device 35 may be configured to receive input from the user regarding the accessed medication dispensing information related to a selected patient. FIG. 7, Block 300. For example, the display device 30 may present a list of patients under the user's care, and the user may in turn select one of the patients to view his or her prescriptions to be filled. Access may then be provided to a container configured to receive a plurality of dispensed medications for administering to the selected patient, block 310, and the user may be provided with access to dispense at least one medication stored in the storage device that was prescribed to the selected patient, block 320. In this way, the user may be able to place at least some of the dispensed medications into the container for transporting and administering to the selected patient. For example, in some cases, in providing access to a container, the processor 210 (FIG. 6) may be configured to direct the display device 35 to display a message to the user prompting the user to dispense one of the containers from the container dispensing device. FIG. 7, Block 330.

As the user places each dispensed medication into the container, the receipt of the dispensed medications may be sensed, as described above with reference to FIGS. 4 and 5. FIG. 7, Block 340. Furthermore, the processor 210 may be configured to determine an accuracy of the dispensing transaction based on the receipt of the at least one dispensed medication detected by the sensor. FIG. 7, Block 350. For example, as described above with reference to FIG. 5, each dispensed medication may be associated with an estimated weight. In embodiments wherein the sensor is a scale, the processor may be able to determine whether the total weight of the container with its contents is approximately the same as the calculated estimated weight of a container holding the medications that should have been dispensed. If the weight is not within an acceptable tolerance (e.g., as set by the user), then the processor 210 may direct the display device 35 to alert the user as to the discrepancy and prompt the user to check the dispensed medications for accuracy. With respect to the embodiments wherein the sensor is a barcode or RFID reader, if the scanned medication does not match the medication that should have been dispensed, the user may similarly be alerted to the potential error in dispensing.

In some embodiments, the system 200 further includes a printing device 70 in communication with the processor 210. As described above, the printing device 70 may be configured to print a summary of a selected dispensing transaction, and the summary may include at least one detail relating to the selected dispensing transaction. In other words, the summary may provide the information necessary to identify and distinguish medications carried in one container (for one patient) from medications carried in another container (for another patient). Thus, the summary of the medication dispensing information related to the selected patient may be printed, as depicted in FIG. 7 at block 360 (e.g., automatically, such as at the conclusion of a dispensing transaction, or upon the request of a user received at the user input device). As noted above, the summary may be in the form of a label and/or a receipt.

In this way, when a user wishes to dispense medications for more than one patient, one or more of the steps provided in FIG. 7 may be performed for the first selected patient (e.g., during the first dispensing transaction). At the conclusion of the first dispensing transaction, the user may select a second patient for whom to dispense medications, and one or more of the steps shown in FIG. 7 may likewise be performed for the second selected patient using a second container. The user may do this for as many patients as required, the result being that the user would have a separate container for securely transporting the medications for each selected patient. Thus, medications for different patients would remain separate and clearly identified, minimizing the risk of co-mingling and inaccurate administering to the patients.

In addition, in cases where the number/volume of medications dispensed in a single dispensing transaction do not fit in a single container, the user may be able to request access to additional containers, as well as additional summaries (e.g., labels and receipts) to be associated with the additional containers. In this regard, each container may be able to hold between approximately 10 and 15 medications, depending on the size and shape of the dispensed medications.

In addition to the benefits described above, the use of separate containers to securely transport medications for different patients provides the further benefit of facilitating the return of medications from the patient's room to the storage device from which it was dispensed, such as in the event that a patient refuses to take a prescribed medication, for example. Such containers may also be used for transporting medications that are to be wasted or restocked in other storage devices (e.g., not necessarily the storage device from which it was dispensed). Accordingly, those skilled in the art in light of this disclosure would recognize that embodiments of the described storage devices, systems, methods, and computer program products may be useful for providing containers to securely transport medications and medical accessories between any two points, in addition to between the storage device and a selected patient.

Exemplary embodiments of the present invention have been described above with reference to block diagrams and flowchart illustrations of methods, apparatuses (e.g., systems) and computer program products. It will be understood that each operation, action, step and/or other types of functions shown in the diagram (FIG. 7), and/or combinations of functions in the diagram, can be implemented by various means. Dashed lines in FIG. 7 indicate optional steps of the method. Means for implementing the functions of the flow diagram, combinations of the actions in the diagrams, and/or other functionality of example embodiments of the present invention described herein, may include hardware and/or a computer program product including a computer-readable storage medium (as opposed to or in addition to a computer-readable transmission medium) having one or more computer program code instructions, program instructions, or executable computer-readable program code instructions stored therein.

For example, program code instructions associated with FIG. 7 may be stored on one or more storage devices, such as a memory 220, and executed by one or more processors, such as processor 210, shown in FIG. 6. Additionally or alternatively, one or more of the program code instructions discussed herein may be stored and/or performed by distributed components, such as those discussed in connection with system 200. As will be appreciated, any such program code instructions may be loaded onto computers, processors, other programmable apparatuses or network thereof from one or more computer-readable storage mediums to produce a particular machine, such that the particular machine becomes a means for implementing the functions of the actions discussed in connection with, e.g., FIG. 7 and/or the other drawings discussed herein. As such, FIG. 7 showing data flows may likewise represent program code instructions that may be loaded onto a computer, processor, other programmable apparatus or network thereof to produce a particular machine.

The program code instructions stored on the programmable apparatus may also be stored in a nontransitory computer-readable storage medium that can direct a computer, a processor (such as processor 210) and/or other programmable apparatus to function in a particular manner to thereby generate a particular article of manufacture. The article of manufacture becomes a means for implementing the functions of the actions discussed in connection with, e.g., FIG. 7. The program code instructions may be retrieved from a computer-readable storage medium and loaded into a computer, processor, or other programmable apparatus to configure the computer, processor, or other programmable apparatus to execute actions to be performed on or by the computer, processor, or other programmable apparatus. Retrieval, loading, and execution of the program code instructions may be performed sequentially such that one instruction is retrieved, loaded, and executed at a time. In some example embodiments, retrieval, loading and/or execution may be performed in parallel by one or more machines, such that multiple instructions are retrieved, loaded, and/or executed together. Execution of the program code instructions may produce a computer-implemented process such that the instructions executed by the computer, processor, other programmable apparatus, or network thereof provides actions for implementing the functions specified in the actions discussed in connection with, e.g., the process illustrated in FIG. 7.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A storage device for dispensing medications, wherein the storage device is configured to dispense medications during multiple dispensing transactions conducted for a single user during a single interaction, wherein each dispensing transaction is associated with a particular selected patient, the storage device comprising:
    a plurality of drawers defined by the storage device and configured to store a plurality of medications;
    a display device associated with the storage device and configured to present medication dispensing information related to a selected patient;
    a user input device associated with the storage device and configured to receive input from a user regarding at least one dispensing transaction; and
    a container dispensing device supported by the storage device and configured to store and dispense containers, wherein each container is configured to receive a plurality of dispensed medications for administering to a single selected patient,
    wherein each container is configured to allow secure transport of the dispensed medications received therein between the storage device and the selected patient.

2. The storage device of claim 1 further comprising a printing device configured to print a summary of a selected dispensing transaction, wherein the summary comprises at least one detail relating to the selected dispensing transaction.

3. The storage device of claim 2, wherein the at least one detail relating to the selected dispensing transaction is selected from the group consisting of a name of the selected patient, a birth date of the selected patient, a location of the selected patient, a date of the selected dispensing transaction, a time of the selected dispensing transaction, and a listing of the dispensed medications received within the container.

4. The storage device of claim 2, wherein the summary is embodied by a label comprising a printed surface and an adhesive surface, and wherein the adhesive surface is configured to be applied to an outer surface of the container.

5. The storage device of claim 4, wherein each container comprises a bag, and wherein the label is configured to be applied to the bag so as to seal the medications received therein.

6. The storage device of claim 2, wherein the summary is embodied by a receipt, and wherein each container is configured to receive the receipt therein.

7. The storage device of claim 1, wherein each container is made of a translucent material.

8. The storage device of claim 1, wherein each container defines an open end, and wherein the open end is sealable onto itself.

9. The storage device of claim 1 further comprising a sensor configured to detect receipt of the dispensed medications within the container.

10. The storage device of claim 1, wherein at least one of the dispensed medications is a medical accessory.

11. A system for dispensing medications comprising:
    a processor configured to direct the dispensing of medications from a storage device during at least one dispensing transaction conducted for a single user during a single interaction, wherein each dispensing transaction is associated with a particular selected patient, wherein the processor is further configured to access medication dispensing information related to the selected patient;

a display device in communication with the processor and configured to present to the user at least one detail from the accessed medication dispensing information;

a user input device in communication with the processor and configured to receive input from the user regarding the accessed medication dispensing information; and a sensor in communication with the processor and configured to detect receipt of at least one dispensed medication within a container, wherein each container is configured to receive a plurality of dispensed medications for administering to the selected patient, wherein each container is configured to allow secure transport of the dispensed medications received therein from a storage device, from which the medication was dispensed, to the selected patient, and wherein the processor is configured to determine an accuracy of the dispensing transaction based on the receipt of the at least one dispensed medication detected by the sensor.

12. The system of claim 11 further comprising a printing device in communication with the processor and configured to print a summary of a selected dispensing transaction, wherein the summary comprises at least one detail relating to the selected dispensing transaction.

13. The system of claim 12, wherein the summary is embodied by a label comprising a printed surface and an adhesive surface, and wherein the adhesive surface is configured to be applied to an outer surface of the container.

14. The system of claim 13, wherein each container comprises a bag, and wherein the label is configured to be applied to the bag so as to seal the received medications therein.

15. The system of claim 12, wherein the summary is embodied by a receipt, and wherein each container is configured to receive the receipt therein.

16. A method of dispensing medications comprising:

receiving input regarding medication dispensing information related to a selected patient via a user input device;

providing access to a container configured to receive a plurality of dispensed medications for administering to the selected patient; and providing a user with access to dispense at least one medication stored in a storage device and prescribed to the selected patient such that the user is able to place at least some of the dispensed medications into the container for administering to the selected patient, wherein each container is configured to allow secure transport of the dispensed medications received therein from the storage device to the selected patient, and wherein the step of providing access to a container comprises prompting the user to dispense one of a plurality of containers from a container dispensing device.

17. The method of claim 16 further comprising the step of printing a summary of the medication dispensing information related to the selected patient.

18. The method of claim 16 further comprising the step of sensing the receipt of the dispensed medications into the container.

19. The method of claim 18 further comprising the step of determining an accuracy of the dispensing transaction based on the sensed receipt of the dispensed medications.

20. A computer program product comprising at least one computer-readable storage medium having computer-readable program code portions stored therein, the computer-readable program code portions comprising:

a first executable portion configured for receiving input regarding medication dispensing information related to a selected patient via a user input device;

a second executable portion configured for providing access to a container configured to receive a plurality of dispensed medications for administering to the selected patient;

a third executable portion configured for providing a user with access to dispense at least one medication stored in a storage device and prescribed to the selected patient such that the user is able to place at least some of the dispensed medications into the container for administering to the selected patient;

a fourth executable portion configured for sensing the receipt of the dispensed medications into the container; and a fifth executable portion configured for determining an accuracy of the dispensing transaction based on the sensed receipt of the dispensed medications, wherein each container is configured to allow secure transport of the dispensed medications received therein from the storage device to the selected patient.

21. The computer program product of claim 20, wherein the second executable portion is configured for prompting the user to dispense one of a plurality of containers from a container dispensing device.

22. The computer program product of claim 20 further comprising a fourth executable portion configured for printing a summary of the medication dispensing information related to the selected patient.

* * * * *